United States Patent [19]

Fink

[11] Patent Number: 4,960,412
[45] Date of Patent: Oct. 2, 1990

[54] CATHETER INTRODUCING SYSTEM

[75] Inventor: E. David Fink, Schnectady, N.Y.

[73] Assignee: Universal Medical Instrument Corp., Ballston Spa, N.Y.

[21] Appl. No.: 182,138

[22] Filed: Apr. 15, 1988

[51] Int. Cl.⁵ .............................................. A61M 5/18
[52] U.S. Cl. ..................................... 604/167; 604/256
[58] Field of Search ............... 604/167, 169, 164, 165, 604/168, 256, 297; 137/230, 816, 849

[56] References Cited

U.S. PATENT DOCUMENTS

| | | | |
|---|---|---|---|
| 4,000,739 | 1/1977 | Stevens | 604/169 |
| 4,149,535 | 4/1979 | Volder | 604/164 |
| 4,177,814 | 12/1979 | Knepshield et al. | 604/167 |
| 4,424,333 | 1/1984 | Spector et al. | 604/167 |
| 4,430,081 | 2/1984 | Timmermans | 604/167 |
| 4,531,937 | 7/1985 | Yates | 604/164 |
| 4,610,655 | 9/1986 | Matsumoto et al. | 604/167 |
| 4,655,752 | 4/1987 | Honkaner et al. | 604/167 |
| 4,673,393 | 1/1987 | Suzuki et al. | 604/167 |
| 4,798,594 | 1/1989 | Hillstead | 604/167 |

Primary Examiner—C. Fred Rosenbaum
Assistant Examiner—Kathleen Daley
Attorney, Agent, or Firm—Lackenbach Siegel Marzullo & Aronson

[57] ABSTRACT

A catheter introducer valve assembly of a catheter introducer leading to a blood vessel of a patient for positioning at least one catheter tube through the catheter introducer and its sheath to a blood vessel of a patient. The valve assembly unit has first and second valves, the first valve being for preventing or minimizing the flow of blood from the valve assembly unit when the catheter tube is absent from the catheter introducer and the second valve being for preventing or minimizing the flow of blood when the catheter tube is present in the catheter introducer. The first valve, which is made of a flexible, resilient material, is shaped as a disk having a valve slit, such a duckbill valve, positioned diametrically across the passage of the valve assembly body. The rim surface of the valve disk has a slightly smaller diameter than the diameter of the positioning area of the inner surface of the valve assembly body where the valve disk is located so that a cylindrical space is formed therebetween. A pair of opposed holding bosses connected to the disk rim are located in the cylindrical space transverse to the direction of the valve slit. Pressure against the valve disk by any flow of blood is resisted by the pressure of the holding bosses against the inner surface of the positioning area so that the lips of the valve are kept pressed together to shut off or minimize the flow of blood. Also, the holding bosses help to close the lips of the valve during the withdrawal procedure of the catheter tube from the introducer assembly.

11 Claims, 2 Drawing Sheets

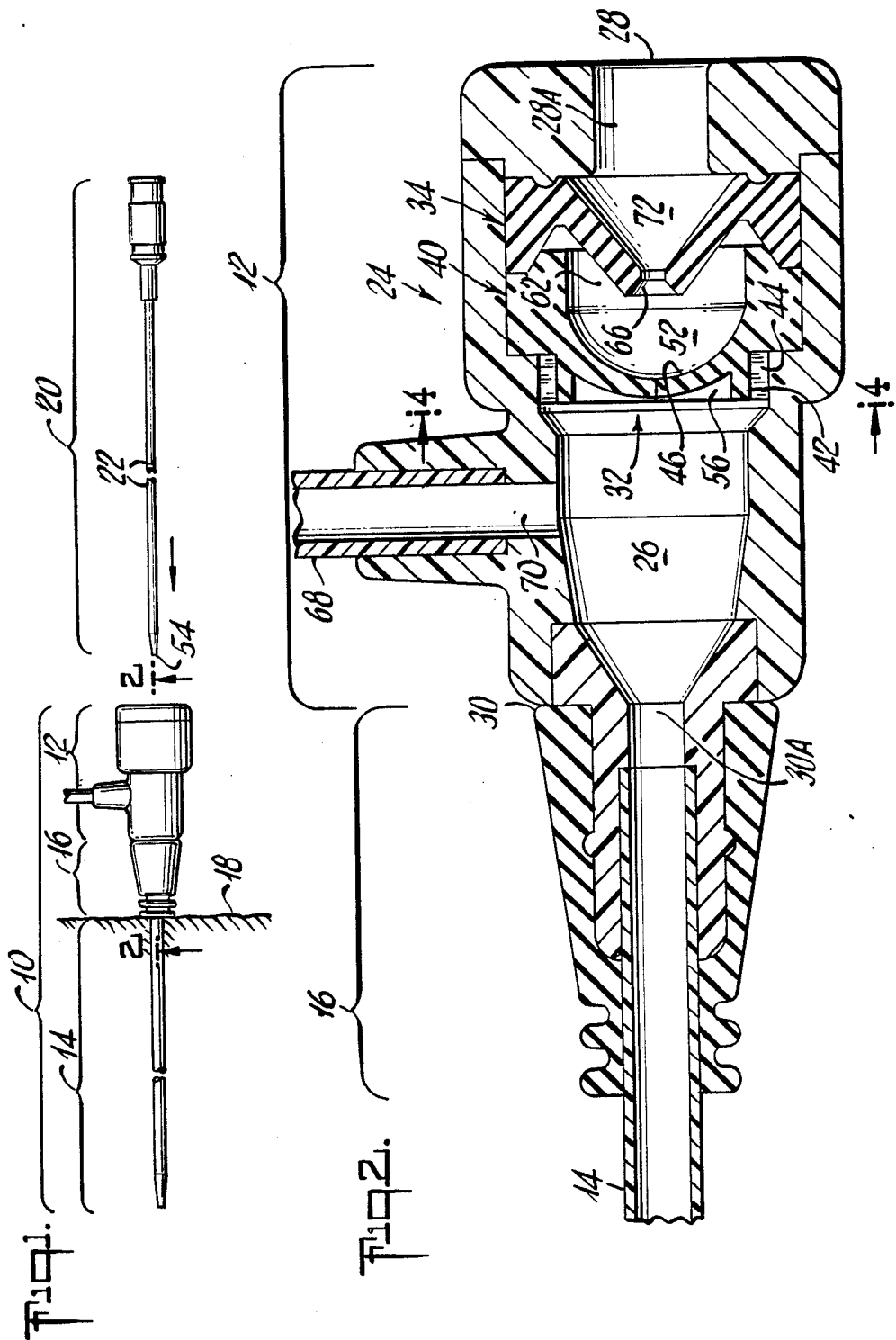

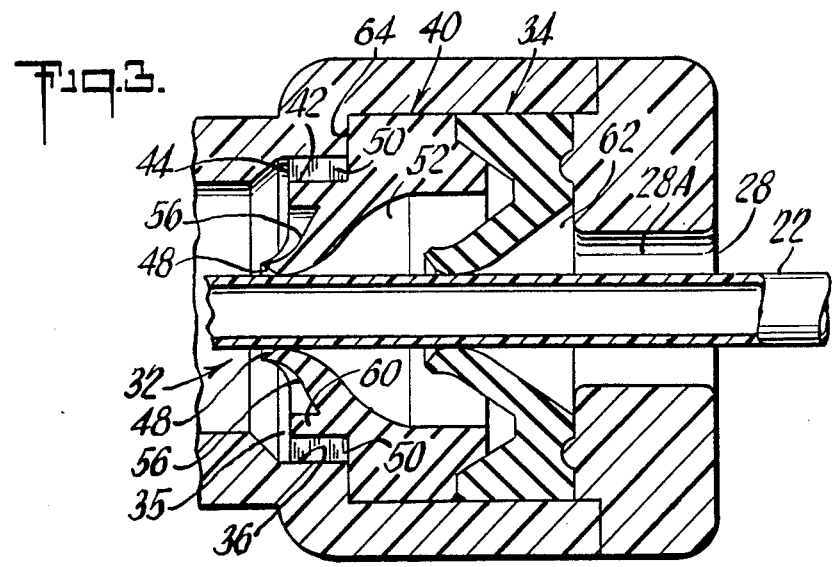
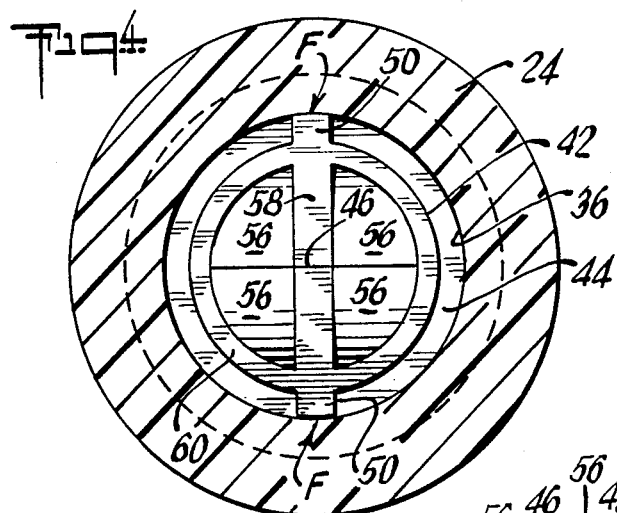
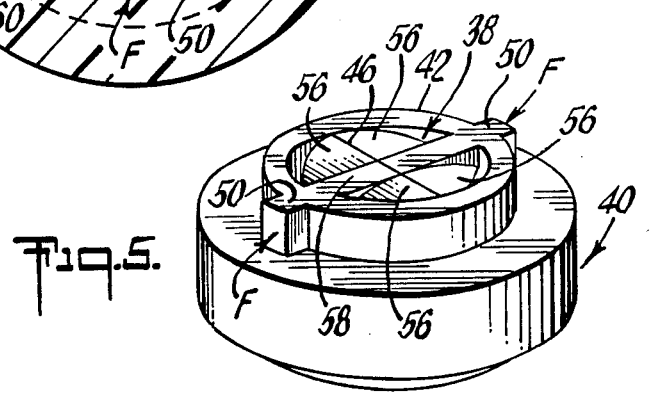

CATHETER INTRODUCING SYSTEM

FIELD OF THE INVENTION

This invention relates generally to percutaneous catheter introducers and more specifically to the valve assembly for catheter introducers.

BACKGROUND OF THE INVENTION

Catheter introducers in percutaneous procedures are placed in a vein or artery of a patient in accordance with various procedures known in the art. A catheter introducer typically includes a long sheath that has a distal end positioned in the vein or artery and a proximal end positioned immediately external to the epidermis. The catheter introducer also includes a valve assembly positioned at the proximal end of the sheath. After the catheter introducer is mounted in accordance with the insertion procedure, generally several catheter tubes are exchanged, one replacing the other, each one being passed through the catheter introducer into the vein or artery and thereupon directed by the doctor to its final destination.

A primary concern prior to the insertion of the catheter tube into the catheter introducer both during the time the catheter tube is positioned in the introducer and after the removal of the catheter tube from the introducer is blood loss, and more particularly excessive blood loss.

One type of introducer valve assembly includes two valves. This type is described in U.S. application Ser. No. 760,817, filed Jul. 31, 1985, entitled "Self-sealing Percutaneous Tube Introducer", allowed on May 14, 1986. The first internal valve seals off any passage of blood from the sheath of the introducer during the time the catheter tube is not present in the introducer. The second external valve seals around the catheter tube during and after the insertion of the catheter tube into the introducer so as to seal off any passage of any blood present in the sheath around the outer surface of the catheter tube. The second valve is typically a valve with a small thru-hole.

This invention is directed to the first valve. The first valve is directed to accomplishing the primary purpose of shutting off the flow of blood in the sheath when the catheter tube is absent, but it must also be adapted to easily allow passage of the catheter tube during the insertion procedure. These two functions are fundamentally contrary and thus present a basic problem.

The introducer described in U.S. application Ser. No. 760,817 has the first and second valves in the valve assembly placed upstream and downstream, respectively, relative to the blood flow, that is internally and externally with respect to the patient. The first valve is made of a resilient, flexible material such as rubber and has three triangularly configured slits meeting at the axis of the valve forming three flaps. The slits easily open as the catheter tube is passed through the introducer during the insertion procedure, and further resiliently close to shut off any blood flow when the catheter tube is not present. Although the triangular flaps close off the interior of the introducer valve assembly when the catheter tube is not present, it can be said that the closing of the triangular shaped flaps is somewhat imperfect against the pressure of blood escaping from the vein or artery, so that some leakage of blood can occur.

OBJECTS OF THE INVENTION

It is therefore an object of this invention to provide a catheter introducer that consistently seals off the flow of blood from an artery or vein of a patient when the catheter tube is not present.

It is another object of this invention to provide a catheter introducer that includes a valve that effectively seals of the flow of blood from an artery of vein of a patient when the catheter tube is not present in the introducer assembly and also provides easy passage for the catheter tube during the insertion procedure of the catheter tube.

It is another object of this invention to provide a catheter introducer of the type having two valves with one valve effectively sealing off the flow of blood from a vein or artery when the catheter tube is not present in the introducer assembly and the other valve sealing off the flow of blood when the catheter tube is present in the introducer assembly.

It is still another object of this invention to provide a catheter introducer which both seals off the flow of blood from the patient when the catheter tube is absent and also easily expands so as to seal around a wide range of catheter tube diameters.

It is still another object of this invention to provide a catheter introducer that can be placed in a patient's blood vessel and that will accept catheters of various sizes through it without fear of excessive blood loss.

SUMMARY OF THE INVENTION

In accordance with these and other objects which will become apparent hereinafter, there is provided a catheter introducer valve assembly unit for positioning a catheter tube through the catheter introducer and its sheath to a blood vessel of a patient. The valve assembly unit has first and second valves, the first valve for preventing or minimizing the flow of blood from the valve assembly unit when the catheter tube is absent from the catheter introducer and the second valve for positioning the catheter and preventing or minimizing the flow of blood when the catheter tube is present in the catheter introducer. The first valve, which is made of a flexible, resilient material, is shaped as a disk having a valve slit, such as a duckbill valve, positioned diametrically across the passage of the valve assembly body. The rim surface of the valve disk has a slightly smaller diameter than the diameter of the positioning area of the inner surface of the valve assembly body where the valve disk is located so that a cylindrical space is formed therebetween. A pair of opposed holding bosses connected to the valve disk transverse, or normal, to the direction of the valve slit are located in the cylindrical space. Pressure against the valve disk by any flow of blood is resisted by the pressure of the holding bosses against the inner surface of the positioning area so that the lips of the valve are kept pressed together to shut off the flow of blood. Also, the holding bosses help to close the lips of the valve immediately after the withdrawal of the catheter tube from the first valve during the withdrawal procedure of the catheter tube from the catheter introducer assembly.

U.S. patents generally relating to the invention herein are as follows:

U.S. Pat. No. 584,091 issued June 8, 1987 to Leidich.
U.S. Pat. No. 2,524,764 issued Oct. 10, 1950 to Burke.
U.S. Pat. No. 3,577,992 issued May 11, 1971 to Merry et al.

U.S. Pat. No. 4,000,739 issued Jan. 4, 1977 to Stevens.

U.S. Pat. No. 4,424,833 issued Jan. 10, 1984 to Spector et al.

U.S. Pat. No. 4,439,081 issued Feb. 7, 1984 to Timmermans.

The present invention will be better understood and the objects and important features, other than those specifically enumerated above, will become apparent when consideration is given to the following details and description, which when taken in conjunction with the annexed drawings, describes, discloses, illustrates, and shows a preferred embodiment or modification of the present invention and what is presently considered and believed to be the best mode of practice in the principles thereof.

BRIEF DESCRIPTION OF THE DRAWINGS

FIG. 1 illustrates a catheter introducer assembly in the body of a patient with a catheter tube about to be introduced into the introducer assembly;

FIG. 2 is a cross-sectional view of the introducer assembly particularly of the introducer valve assembly illustrated in FIG. 1 taken through line 2—2;

FIG. 3 is a fragmented cross-sectional view of the introducer valve assembly similar to the view illustrated in FIG. 2 with the catheter tube in position in the introducer valve assembly;

FIG. 4 is a cross-sectional view of the introducer valve assembly taken through line 4—4 in FIG. 2; and FIG. 5 is an perspective view taken in isolation of the base of a duck-bill valve in the introducer valve assembly showing its reinforcing rib.

DESCRIPTION OF THE PREFERRED EMBODIMENT

Reference is now made in detail specifically to the drawings in which identical or similar parts are designated by the same reference numerals throughout the various views.

A catheter introducer assembly 10 illustrated in FIG. 1 includes a catheter introducer valve assembly 12, a sheath tube 14, and a sheath connector 16 with sheath 14 shown positioned in the body of a patient and valve assembly 12 and a flexible sheath collar 16 positioned external to the skin 18. Sheath tube 14 has been introduced into the body of the patient in a manner known in the art. A catheter 20 includes a catheter tube 22 illustrated about to be introduced into valve assembly 12 for final positioning in the blood vessel of the patient, that is, in either a vein or an artery. As illustrated in FIG. 2, valve assembly 12 includes a generally cylindrical assembly body 24 having a central passage 26 having inlet and outlet ends 28 and 30, respectively, where an inlet port 28A and an outlet port 30A, respectively, are located.

A first valve 32 positioned across passage 26 in assembly body 24 seals off any flow of blood from the blood vessel during the time catheter tube 22 is absent from catheter introducer assembly 12 as is the case in FIG. 2. A second valve or centering gasket 34 is positioned across passage 26 in assembly body 24 seals off any flow of blood from the blood vessel during the time catheter tube 22 is positioned or is being positioned in catheter introducer assembly 10 as is illustrated in FIG. 3. Second valve 34 is positioned between first valve 32 and inlet end 28 downstream of first valve 32 relative to any blood flow from the blood vessel.

Valve body 24 has a cylindrical compartment 35, in axial alignment with passage 26, which has a diameter slightly greater than the diameter of passage 26 and having a cylindrical inner surface 36. First valve 32 includes a generally cylindrical disk 38 and a mounting, or positioning, ring 40 integrally connected to disk 38 or external to disk 38. Disk 38, which is illustrated in cross-section in FIGS. 3 and 4 and in perspective isolation is FIG. 5, has a disk diameter slightly less then the diameter of cylindrical compartment 35 at inner surface 36 so that a small cylindrical space 44 is defined by inner disk rim 42 and cylindrical inner surface 36.

First valve 32 is made of a flexible, resilient material such as carbon blackened natural rubber, elastomer, synthetic rubber, or neoprene. Disk 38 has a diametrically positioned valve slit 46 having opposed valve lips 48. Valve slit 46 is shown in its closed position in FIG. 2 and in its forced open position in FIG. 3 with catheter tube 22 positioned between lips 48, which have been pressed apart. Valve slit 46 is known in the art as a slit, or duckbill, valve.

A pair of diametrically opposed holding bosses 50 are connected to disk inner cylindrical rim 42 and are positioned in cylindrical space 44 positioned transverse, or normal, to valve slit 46. Holding bosses 50 have curved outer ends conformed to the configuration of and in tight contact with cylindrical inner surface 36 of valve body 24 so that holding bosses 50 keep first valve 32 in a fully sealed position when catheter tube 22 is absent from catheter introducer assembly 10 as illustrated in FIG. 2. In particular, when any blood present within passage 26 exerts lateral pressure against disk 38 and valve lips 48, valve lips 48 exert a radial outward pressure along the wall of disk 38, which radial outward pressure is transmitted to holding bosses 50, which in turn are pressed against cylindrical inner surface 36. Because of the tight fit between holding bosses 50 and cylindrical inner wall 36, the outward pressure is resisted, indicated by inwardly directed arrows F in FIGS. 4 and 5, with the result that valve lips 48 are held together in sealing relationship so that leakage of blood is minimized or prevented. Also, holding bosses 50 help to reliably close valve lips 48 immediately after the withdrawal of catheter tube 22, in particular of tip 54 (FIG. 1), past valve lips 48 during the withdrawal procedure of catheter tube 22 from catheter introducer assembly 10.

First valve 32 has a coned recess 52 which opens toward inlet end 28 for guiding tip 54 of catheter tube 22 to valve slit 46 during the introduction procedure of catheter tube 22 into catheter introducer assembly 10. Recess 52 is formed within both disk 38 and positioning ring 40.

Valve disk 38 has opposed outer and inner faces, which are oriented towards inlet and outlet ends 28 and 30, respectively, of assembly body 24, the outer end face forming part of coned recess 52. The inner end face is curved in general conformity with coned recess 52 so that a pair of arced recesses 56 are formed. A diametrical reinforcing rib 58 defined by arced recesses 56 extends across the inner end face of disk 38. A circumferential ring 60 is defined around the inner end face between rim 42 and arced recesses 56. Diametrical rib 58 extends between valve lips 48 and ring 60 in alignment with holding bosses 50. Rib 58 and ring 60 are stiffeners for valve disk 38 in association with holding bosses 50 with the resistance F to any opening of valve slit 46 by outward movement of valve lips 48 being passed to and resisted by holding bosses 50 being directed along rib 58 via ring 60.

Assembly body 24 has a cylindrical mounting compartment 62 extending between inlet port 28A and cylindrical compartment 35. Positioning ring 40 is set in mounting compartment 62 so as to seat first valve 32 to prevent axial and radial movement of first valve 32. The outer cylindrical surface of positioning ring 40 is flush with the inner cylindrical surface of mounting compartment 62. The upstream side of positioning ring 40 is flush with the ringed shoulder 64 formed between mounting compartment 62 and cylindrical compartment 35.

Second valve 34, which is illustrated as being configured in the general shape of a disk, is tightly positioned in mounting compartment 62 between inlet end 28 of valve body 24 and positioning ring 40 downstream of first valve 32 so that both first and second valves 32 and 34 are prevented from axial and radial displacement. The cylindrical outer rim of second valve 34 is flush with the inner cylindrical surface of mounting compartment 62. Second valve 34 is made of a flexible, resilient material. The center of the disk of second valve or gasket 34 has a small circular hole 66 through which catheter tube 22 passes during the introduction and final positioning of catheter tube 22 in catheter introducer assembly 10. Hole 66 is smaller in diameter than the diameter of catheter tube 22 so that second valve 34 seals off the outer surface of catheter tube 22 so as to minimize or prevent the outward flow of any blood present in passage 26 during the presence of catheter tube 22 in introduction assembly 10. A coned recess 72 opening toward inlet port 28A aids in guiding tip 52 of catheter tube 22 to hole 66. Second valve 34 is a Lip-Seal TM valve of the type known as a thru-hole valve.

A second inlet, or sidearm, tube 68 opening at an inlet port upstream from first valve 32 has opening and closing apparatus (not shown) at its end. Optional medicaments can be introduced into passage 26 through tube 68.

Although the embodiments illustrated in the drawings and described herein demonstrate several embodiments possible within the framework of the invention, it will be apparent to those skilled in the art that other alternate constructions or modifications may be made by one having ordinary skill in the art without necessarily departing from the spirit or scope of the invention.

What is claimed is:

1. A catheter introducing valve assembly of a catheter introducer including a sheath tube positioning a catheter tube in a blood vessel of a patient, comprising in combination, a valve assembly including a central passage having opposed inlet and outlet ends, said valve assembly for positioning the catheter tube which is introduced into said valve assembly at said inlet end;

first valve means bearing sealing lips of flexible, resilient material positioned internally across said passage in said valve assembly for sealing off flow of blood during any time the catheter tube is absent from the catheter introducer, second valve means positioned externally across said passage in said valve assembly and comprising gasket means with an aperture adapted to the diameter of the sheath tube for sealing off flow of blood during the time the catheter tube is positioned in the catheter introducer, holding means connected to said first valve means and adapted to said valve assembly for keeping said first valve means in a sealed position when the catheter tube is absent, connector means mounted to said valve assembly at said outlet end for securing the sheath tube to said valve assembly;

said first valve means comprising a first valve body made of a flexible, resilient material, and including a reinforced valve disk having a centrally positioned valve slit extending transversely to said central passage, said valve slit having opposed valve lips; and said holding means being positioned transversely to said valve slit so as to keep said valve lips together when the catheter tube is absent from the catheter introducer and to close said valve lips during withdrawal of the catheter tube;

and said valve assembly further including a generally cylindrical assembly body having a generally cylindrical compartment area in axial alignment with a central passage having an inner surface, said compartment area having a first diameter; said reinforced valve disk having a cylindrical disk rim of a second diameter, said second diameter being slightly less than said first diameter, wherein a cylindrical space is defined between said disk rim and said inner surface of said compartment area; and wherein said holding means includes a pair of diametrically opposed peripheral bosses connected to said disk rim and positioned transversely to said valve slit, said bosses having curved ends conforming to the configuration of and in tight contact with said inner surface of said compartment area, whereby even pressure is exerted against said valve lips, the lips are held together in sealing relationship during the absence of the catheter tube from the catheter tube assembly.

2. The valve assembly according to claim 1, wherein said first valve means comprises a cylindrical positioning ring connected to said first valve means, said positioning ring having a diameter greater than said second diameter, said valve assembly including a cylindrical positioning compartment external to said cylindrical compartment area, said positioning ring being seated in said positioning compartment so as to prevent movement of said first valve means.

3. The valve assembly according to claim 2, wherein said positioning ring is external to said valve disk when seated in the positioning compartment.

4. The valve assembly according to claim 2, wherein said first valve means includes an arced recess which opens toward said inlet end for guiding said catheter tube to said valve slit during the introduction of said catheter tube into said catheter introducer assembly.

5. The valve assembly according to claim 4, wherein said valve disk has opposed inner and outer surfaces facing said outlet and inlet ends, respectively, of said assembly body, said inner end surface being curved in general conformity with said arced recess means so as to define a reinforcing rib diametrically extending to said disk rim in operative association with said pair of bosses.

6. The valve assembly according to claim 2, wherein said inner surface further includes a circumferential ring defined by said valve rim and said arced recess.

7. The valve assembly according to claim 2, wherein said second valve means is positioned in said cylindrical positioning compartment in tight association with and downstream of said first valve body.

8. The valve assembly according to claim 1, wherein said first valve means is a duckbill valve.

9. The valve assembly according to claim 1, wherein said first valve is made of a flexible, resilient material.

10. The valve assembly according to claim 1, wherein said connector means is a flexible connector tube.

11. The valve assembly as in claim 4, wherein the second valve means is in the form of a conical centering gasket.

* * * * *